United States Patent [19]
Wong et al.

[11] Patent Number: 5,938,654
[45] Date of Patent: *Aug. 17, 1999

[54] OSMOTIC DEVICE FOR DELAYED DELIVERY OF AGENT

[75] Inventors: Patrick S.-L. Wong, Palo Alto; Felix Theeuwes; James B. Eckenhoff, both of Los Altos; Steven D. Larsen, Dublin; Hoa T. Huynh, Fremont, all of Calif.

[73] Assignee: Alza Corporation, Palo Alto, Calif.

[ * ] Notice: This patent is subject to a terminal disclaimer.

[21] Appl. No.: 08/382,947

[22] Filed: Feb. 1, 1995

Related U.S. Application Data

[63] Continuation of application No. 07/871,465, Apr. 20, 1992, abandoned, which is a continuation-in-part of application No. 07/745,822, Aug. 16, 1991, abandoned, which is a continuation-in-part of application No. 07/648,270, Jan. 30, 1991, abandoned, and a continuation-in-part of application No. 07/701,927, May 17, 1991, Pat. No. 5,110,597, which is a continuation of application No. 07/495,825, Mar. 19, 1990, Pat. No. 5,023,088, which is a continuation-in-part of application No. 07/283,772, Dec. 13, 1988, abandoned, which is a continuation-in-part of application No. 07/270,730, Nov. 14, 1988, abandoned, which is a continuation-in-part of application No. 07/066,905, Jun. 25, 1987, abandoned.

[51] Int. Cl.⁶ .................................................. A61K 9/22
[52] U.S. Cl. .................. 604/892.1; 604/131; 604/891.1; 424/438; 424/453; 424/472
[58] Field of Search .............................. 604/890.1, 892.1, 604/891.1, 93, 131; 424/473, 452, 453, 472, 438; 220/306, 352

[56] References Cited

U.S. PATENT DOCUMENTS

| | | | |
|---|---|---|---|
| 2,266,270 | 12/1941 | Roth | 220/352 |
| 3,258,115 | 6/1966 | Kath | 220/352 |
| 3,732,865 | 5/1973 | Higuchi et al. | 128/260 |
| 3,845,770 | 11/1974 | Theeuwes et al. | 128/130 |
| 3,865,108 | 2/1975 | Hartop | 128/260 |
| 3,995,631 | 12/1976 | Higuchi et al. | 128/260 |
| 4,002,173 | 1/1977 | Manning et al. | 128/296 |
| 4,034,756 | 7/1977 | Higuchi et al. | 128/260 |
| 4,111,202 | 9/1978 | Theeuwes | 128/260 |
| 4,207,893 | 6/1980 | Michaels | 128/260 |
| 4,265,874 | 5/1981 | Bonsen et al. | 424/15 |
| 4,320,759 | 3/1982 | Theeuwes | 128/260 |
| 4,327,725 | 5/1982 | Cortese et al. | 128/260 |
| 4,340,054 | 7/1982 | Michaels | 604/892.1 |
| 4,449,983 | 5/1984 | Cortese et al. | 604/892 |
| 4,526,938 | 7/1985 | Churchill et al. | 525/415 |
| 4,578,075 | 3/1986 | Urguhart et al. | 604/892.1 |
| 4,595,583 | 6/1986 | Eckenhoff et al. | 424/15 |
| 4,601,896 | 7/1986 | Nugent | 424/36 |
| 4,612,008 | 9/1986 | Wong et al. | 604/892 |
| 4,643,731 | 2/1987 | Eckenhoff | 604/892 |
| 4,663,148 | 5/1987 | Eckenhoff et al. | 424/454 |
| 4,692,433 | 9/1987 | Hostetler et al. | 514/12 |
| 4,874,388 | 10/1989 | Wong et al. | 604/892.1 |
| 4,895,724 | 1/1990 | Cardinal et al. | 604/890.1 |
| 5,017,381 | 5/1991 | Maruyama et al. | 424/472 |
| 5,023,088 | 6/1991 | Wong et al. | 424/473 |

FOREIGN PATENT DOCUMENTS

| | | |
|---|---|---|
| 0384642 | 8/1990 | European Pat. Off. ......... A61K 9/22 |
| 9009168 | 8/1990 | WIPO . |
| WO90/09169 | 8/1990 | WIPO .............. A61K 9/22 |

*Primary Examiner*—Mark Bockelman
*Attorney, Agent, or Firm*—John A. Dhuey; Steven F. Stone

[57] ABSTRACT

A dispenser for use in a fluid environment of use which is capable of the delivery of one or a plurality of discrete active agent-containing units in any desired delivery pattern or profile. It also can provide for the initially delayed delivery of an active agent to the environment of use and for high accuracy in the timing of delivery of the active agent.

10 Claims, 3 Drawing Sheets

OSMOTIC DEVICE FOR DELAYED DELIVERY OF AGENT

RELATED PATENT APPLICATIONS

This application is a continuation of application Ser. No. 07/871,465, filed Apr. 20, 1992 abandoned, which is a continuation-in-part of Ser. No. 07/745,822, filed Aug. 16, 1991 abandoned, which is a continuation-in-part of application Ser. No. 07/648,270, filed Jan. 30, 1991 abandoned, and a continuation-in-part of application Ser. No. 07/701,927, filed May 17, 1991, which issued as U.S. Pat. No. 5,110,597 on Jun. 11, 1991, which application is a continuation of application Ser. No. 07/495,825, filed Mar. 19, 1990, which issued as U.S. Pat. No. 5,023,088 on Jun. 11, 1991, which is a continuation-in-part of application Ser. No. 07/283,772, filed on Dec. 13, 1988, now abandoned, which in turn is a continuation-in-part of application Ser. No. 07/270,730, filed on Nov. 14, 1988, now abandoned, which in turn is a continuation-in-part of application Ser. No. 07/066,905, filed on Jun. 25, 1987, now abandoned; and benefit of the filing dates of said earlier filed applications is claimed under 35 U.S.C. § 120.

This application is related to coassigned U.S. Pat. Nos. 4,874,388 issued Oct. 17, 1989 and 4,957,494 issued Sep. 18, 1990.

FIELD OF THE INVENTION

This invention relates to patterned drug delivery. More particularly, this invention is related to osmotically-activated devices for dispensing active agents to a biological environment of use following an initial delay.

BACKGROUND OF THE INVENTION

The concept of patterned drug delivery covers a broad range of systems from time release capsules whose components have coatings which erode at different rates, to controlled release-rate tablets which operate by osmosis.

Osmotic dispensing devices for delivery of therapeutically active agents are well known in the art. Such devices use an expansion means to deliver an agent to an environment of use over a period of hours, days or months. The expansion means absorbs liquid, expands, and acts to drive out beneficial agent formulation from the interior of the device in a controlled, usually constant manner. The osmotic expansion means is used to controllably, usually relatively slowly, and over a period of time, deliver the agent. Thus, these devices are not generally used to delay the initial release of the agent, followed by the rapid release, or substantially simultaneous introduction, of all of the agent or all of the dosage form(s) containing the agent into the environment of use at one time.

The delay of the initial release of an agent has primarily been previously effected by coating the agent or a formulation containing the agent with a dissolvable or bioerodible coating layer, such as gelatin, which coating dissolves or erodes in the environment of use to then make the agent available. Delayed initial release has also been provided by dispersing the agent in a dissolvable or erodible matrix. However, such systems are often unreliable and release cannot be controlled with great accuracy due to the variability and relatively uncontrollable nature of erosion and dissolution.

Therefore, despite the development of the art, there remains a continuing need for improved methods and systems for providing a delayed initial delivery of an active agent to an environment of use that are reliable and that can be programmed to deliver the agent after a particular interval with increased accuracy.

SUMMARY OF THE INVENTION

The present invention is directed to a fluid-imbibing dispensing device for the initially delayed delivery of an active agent to a fluid environment of use. The dispenser comprises a housing open at one end to provide outlet means therefor, at least a portion of the housing proximate the end opposite the outlet means permitting passage of fluid from the environment to the interior of the housing; one active agent unit comprising a container containing an active agent formulation, at least the open end of the active agent unit being disposed within the housing in slidably telescoping arrangement with the outlet means; and, a fluid-activated driving member within the housing in fluid-transmitting relationship with the fluid-passing portion of the housing proximate the end of the housing opposite the outlet means, for separating apart the housing and the active agent unit after exposure to the environment of use. Optionally, the dispenser also comprises a partition layer between the driving member and the open end of the active agent unit.

The invention also is directed to a method for delaying the initial delivery of an active agent to a fluid environment of use, the method comprising placing the dispensing device of the invention into the environment of use, allowing fluid to be imbibed through at least a portion of the housing of the dispensing device for causing the expansion means to expand and exert pressure on the slidably connected housing and active agent unit, and delivering the active agent from the dispensing device by the expansion means increasing in volume, thereby pushing apart and separating the housing and the active agent unit and exposing the active agent formulation to the environment.

BRIEF DESCRIPTION OF THE DRAWINGS

The invention will be described in further detail with reference to the accompanying drawings.

DETAILED DESCRIPTION OF THE INVENTION AND PREFERRED EMBODIMENTS

This invention can provide a variety of drug delivery profiles including, but not limited to, pulsed delivery of a single drug or drug formulation, pulsed delivery of a sequence of different drugs or drug formulations, pulsed delivery of one drug or drug formulation superimposed on continuous delivery of a different drug or drug formulation, pulsed delivery of two drugs or drug formulations simultaneously, simultaneous continuous delivery of several drugs or drug formulations, and the initially delayed delivery of a drug or drug formulation.

In one presently preferred embodiment, the present invention provides a device which is useful for the initial delayed delivery of an active agent formulation to a fluid environment of use, the delivery of the agent formulation from the dispensing device, once begun, being quickly completed rather than being continued over a prolonged period of time. By "prolonged period of time" is meant an extended time period such as for several hours, days, weeks or months. In the present embodiment, in contrast, the delivery device is designed to substantially simultaneously introduce all of the active agent formulation, which formulation can be either an immediate release dosage form or a controlled release dosage form, to exposure to the environment of use substantially at one time after the initial period of delay. This invention provides a sharp pulsed release of active agent with high accuracy.

The dispensing devices of the invention find use, for example, in humans or other animals. The environment of use is a fluid environment and can comprise the stomach, the intestinal tract, or a body cavity such as the peritoneum or vagina. A single dispensing device or several dispensing devices can be administered to a subject during a therapeutic program.

The expressions "active agent" and "drug" are used interchangeably herein and as used refer broadly to any agent, drug, compound, composition of matter or mixture thereof that can be delivered from the system to produce a therapeutic, beneficial or useful result or effect. This includes pesticides, herbicides, germicides, biocides, algicides, rodenticides, fungicides, insecticides, antioxidants, plant growth promoters, plant growth inhibitors, preservatives, antipreservatives, disinfectants, sterilization agents, catalysts, chemical reactants, fermentation agents, foods, food supplements, nutrients, cosmetics, drugs, vitamins, sex sterilants, fertility inhibitors, fertility promoters, air purifiers, microorganism attenuators and other agents that benefit the environment of use.

The terms "active agent" and "drug" as used herein further include any physiologically or pharmacologically active substance that produces a localized or systemic effect or effects in animals, including warm-blooded mammals, humans and primates; avians; domestic household, sport or farm animals such as dogs, sheep, goats, cattle, horses and pigs; laboratory animals such as mice, rats and guinea pigs; fish; reptiles; zoo and wild animals; and the like. The active drug which can be delivered includes inorganic and organic compounds, including, without limitation, those materials that act upon the central nervous system such as hypnotics and sedatives, psychic energizers, tranquilizers, anticonvulsants, muscle relaxants, antiparkinson agents, analgesics, anti-inflammatories, local anesthetics, muscle contractants, antimicrobials, antimalarials, hormonal agents including contraceptives, sympathomimetrics, diuretics, lipid regulating agents, antiandrogenic agents, antiparasitics, neoplastics, antineoplastics, hypoglycemics, nutritional agents and supplements, growth supplements, antienteritis agents, fats, ophthalmics, electrolytes and diagnostic agents.

It is to be understood that more than one active agent may be incorporated into the active agent formulation in a device of this invention, and that the use of the term "agent" or "drug" in no way excludes the use of two or more such agents or drugs. The agents can be in various forms, such as uncharged molecules, components of molecular complexes or nonirritating, pharmacologically acceptable salts. Also, simple derivatives of the agents (such as ethers, esters, amides, etc.) which are easily hydrolyzed by body pH, enzymes, etc., can be employed.

This invention is particularly suited to the delivery of pharmacologically active peptides and protein anabolic hormones such as growth promoting hormones related to the endocrine system comprising, for example, porcine growth promoting hormone, bovine growth promoting hormone, equine growth promoting hormone, ovine growth promoting hormone, human growth promoting hormone, growth promoting hormones derived by extraction and concentration from pituitary and hypothalamus glands, growth promoting hormones produced by recombinant DNA methods, bovine growth promoting hormone as described in Nucleic Acid Res., Vol. 10, p 7197 (1982), ovine growth promoting hormone as described in Arch. Biochem. Biophys., Vol. 156, p 493 (1973), and porcine growth promoting hormone as described in DNA, Vol. 2, pp 37, 45 (1983). Also included are proteins and polypeptides such as growth hormone, somatropin, somatotropin, somatomedin-C, gonadotropic releasing hormone, follicle stimulating hormone, luteinizing hormone, LHRH, growth hormone releasing factor, gonadotropin releasing factor, insulin, calcitonin, colchicine, chorionic gonadotropin, oxytocin, vasopressin, adrenocorticotrophic hormone, epidermal growth factor, fibroblast growth factor, platelet-derived growth factor, transforming growth factor, nerve growth factor, insulin-like growth factor, prolactin, somatostatin, octreotide, cosyntropin, lypressin, thyrotropin releasing hormone, thyroid stimulating hormone, secretin, pancreozymin, enkephalin, glucagon, interleukin-1, interleukin-1 receptor antagonist, interleukin-2, interleukin-3, superoxide dismutase, leukotriene synthesis inhibitors such as lipoxygenase inhibitors, leukotriene antagonists, and the like. Other active agents include colon-targeting mediators of wound healing such as lactic acid or local vasodilators. The active agents and their dosage unit amounts are known to the art in *The Pharmacological Basis of Therapeutics*, by Gilman, Goodman, Rall and Murad, 7th Ed., (1985) published by MacMillan Publishing Co., NY; in *Pharmaceutical Sciences*, Remington, 17th Ed., (1985) published by Mack Publishing Co., Easton, Pa.; and in U.S. Pat. No. 4,526,938.

The term "active agent formulation" as used herein comprises the active agent or drug to be delivered, as a liquid, solid, semisolid or thermosensitive composition, generally in a carrier substance and with or without additional inert ingredients. The term additionally includes an active agent or drug in the from of active agent dosage forms or units.

The terms "drug unit," "dosage unit," "active agent unit" and "active agent dosage unit" as used herein include dosage forms or units that are capable of maintaining their physical configuration and chemical integrity while housed within the dispenser. This includes, without limitation, tablets with or without a density element; matrix tablets; spheres; pellets and elongated tablets where the height-to-diameter ratio exceeds one; capsules; tiny pills, which may be timed-release; elementary osmotic pumps, such as that described in U.S. Pat. No. 3,845,770; mini osmotic pumps, such as those described in U.S. Pat. Nos. 3,995,631, 4,034,756 and 4,111,202; and multichamber osmotic systems referred to as push-pull and push-melt osmotic pumps, such as those described in U.S. Pat. Nos. 4,320,759 and 4,449,983; all of which are incorporated herein by reference. The terms also include a protective container with an active agent formulation or dosage form(s) within it.

As used herein, the expression "external fluid" includes water and other biological fluids.

As used herein, the terms "therapeutically effective" amount or rate refer to the amount or rate of the active agent needed to effect the desired therapeutic, often beneficial, result.

The drug delivery system or dispenser of this invention is designed to deliver one or a plurality of discrete longitudinally aligned individual drug units by the linear expansion of a fluid-activated driving member. The drug units are such that they retain their physical and chemical integrity while contained within the system and do not substantially commence delivery of active agent until after they have been dispensed into the environment. The dispenser is comprised of a dispensing component and a driving component, representative embodiments of which are disclosed herein.

Figure 1:
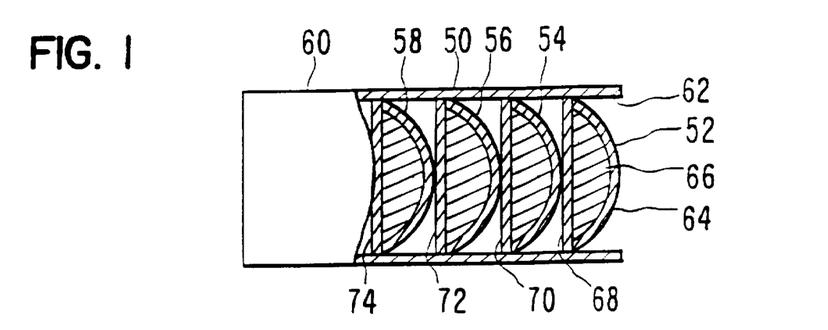
FIG. 1 is a partial cross-sectional view of the dispenser of this invention, illustrating one embodiment of the dispensing configuration.

The dispensing component shown in FIG. 1 is comprised of a housing member 50 and a plurality of discrete drug units 52, 54, 56 and 58 aligned therein. Four drug units are shown; however, the number of units shown is merely illustrative and is not intended to limit the invention in any manner.

The driving member 60 operates to linearly displace the units and dispense them through the exit port 62. The units, 52 for example, are comprised of a preferably fluid-impermeable, such as plastic or polyethylene, container or cap 64 with an active agent formulation or mixture 66 contained or compressed within. While a solid, semi-solid or liquid drug formulation is illustrated, container 64 may alternately contain a plurality of active agent or drug dosage forms, such as mini osmotic pumps, timed-release pills, capsules, spheres, or the like. The containers comprising the units may be bowl-shaped as shown or they may be box-shaped to hold a larger quantity of drug. The units are separated by partition layers 68, 70, 72 and 74, which can be a rigid solid or a gel. As the unit 52 is dispensed through the exit port 62, the drug mixture 66 is exposed to the environment (external fluid) and is thus delivered. Subsequently, the partition layer 68 is dispensed through the exit port 62.

This dispensing configuration provides pulsed drug delivery. As unit 52 is dispensed, a burst of drug is delivered which is followed by another pulse when unit 54 is dispensed and so forth. The units may contain the same drug in the same or different concentrations, or different drugs. In this manner, any pattern of delivery may be fashioned.

Figure 2:
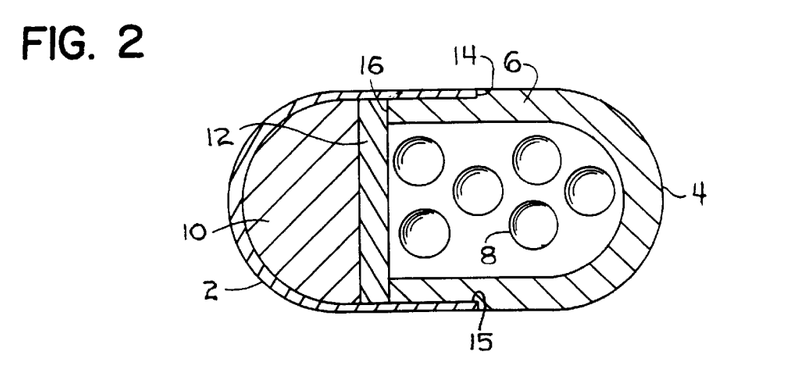
FIG. 2 is a cross-sectional view of another embodiment of the present invention, the device being in closed or prepared form prior to placement in the environment of use.
Figure 3:
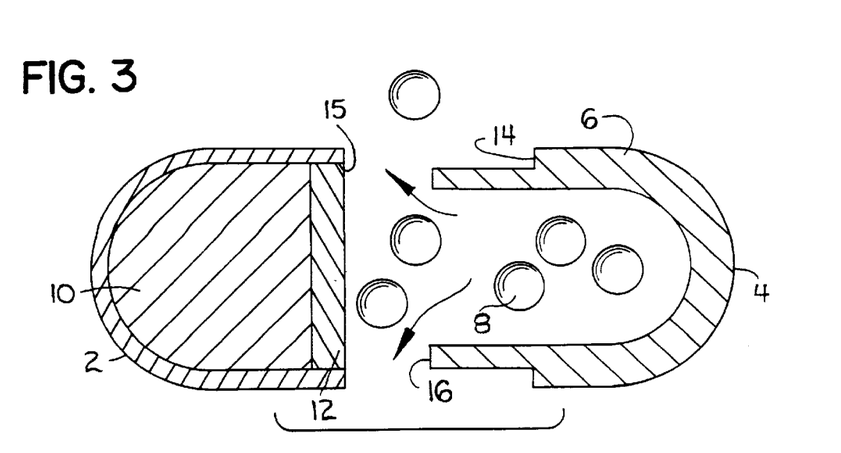
FIG. 3 is the device of FIG. 2 in operation after activation by placement in the environment of use, showing the device opened to release the active agent formulation to the environment.

The dispensing configurations shown in FIGS. 2 and 3 are similar to the dispenser of FIG. 1 except that they include only one drug unit for delivering the active agent to the environment of use, thus providing a single pulse of drug delivery.

FIG. 2 depicts in cross-sectional view one presently preferred embodiment of the delivery device according to the present invention, illustrating both dispensing and driving components. The device is shown in closed or prepared form prior to placement in the environment of use. The dispensing device comprises a housing 2 and one drug unit 4. Drug unit 4 comprises a container or cap 6 containing an active agent formulation, in this embodiment the formulation being a plurality of active agent dosage forms 8. Housing 2 and drug unit 4 are in slidably telescoping arrangement with each other. Housing 2 contains an expansion means or driving member 10 for expanding and for occupying space within the housing. Housing 2 also contains a partition layer 12, which layer 12 is positioned between the agent formulation 8 within container 6 and the driving member 10. Partition layer 12, in a presently preferred embodiment, comprises a composition that is substantially impermeable to the passage of fluid, and it serves to restrict the passage of fluid present in the driving member into that area of drug unit 4 that contains the agent formulation. It operates to essentially maintain the integrity of the active agent formulation and the driving member. Additionally, and importantly, partition layer 12 acts to insure that the expanding driving force generated by the driving member 10 is applied directly against the drug unit 4 to effect the separation of the drug unit from the housing 2. Thus, partition layer 12 must be of sufficient strength, thickness and rigidity to transfer the driving force against the open edge of container 6 of drug unit 4.

Drug unit 4 has an open end with, in this embodiment, a recessed outer edge for forming receiving means 14 for slidably receiving and engaging the exit port 15 of housing 2. The housing and the drug unit at their open ends are close in size and they form a friction fit therebetween. The friction generated is sufficient to maintain the two portions together prior to activation of the expansion means but not so great as to keep the two wall portions from sliding apart once an expanding driving force is exerted. Where additional friction is desired, ridges or other means may be present on one or the other of the contacting surfaces of the housing or the drug unit. Housing 2 and drug unit 4 can be telescoped completely into a closed and continuous external walled position. The open end of drug unit 4 is adapted to fit within the exit port 15 of housing 2. The bottom edge of the open end of drug unit 4 provides a platform or ridge 16 protruding into the compartment formed by housing 2. Ridge 16 is adapted to receive the driving force of the expandable driving member 10, via the partition layer 12, to effect the separation of the drug unit from the housing.

In operation, as the driving member 10 absorbs and imbibes fluid through semipermeable housing 2 from the environment of use, it expands and pushes against partition layer 12, causing the partition layer to slide inside the housing. Partition layer 12 moves toward and contacts ridge 16, pushing against ridge 16 and thus against drug unit 4 to cause the drug unit to slide apart from housing 2 as the driving member 10 continues to expand. This causes the two portions to become separated and the active agent formulations 8 to be exposed to the environment of use, as illustrated in FIG. 3.

FIG. 3 illustrates the dispensing device of FIG. 2 in operation after activation of the device by placement in the environment of use. FIG. 3 shows the device opened to release all of the active agent dosage forms 8 to the environment substantially at the same time. Drug unit 4 comprising container 6 has been separated from housing 2 by the expanding driving force of the driving member 10, which has expanded in size as a result of imbibing fluid from the environment. The arrows in FIG. 3 indicate the exiting of the agent formulation dosage forms 8 from the internal compartment of drug unit 4 through the open end or exit port 15 of housing 2, which is now in communication with the environment.

While the active agent formulation in FIGS. 2 and 3 is shown as a plurality of agent dosage forms, the active agent formulation may alternately be present as a single homogeneous or heterogeneous mass within container 6 and may be in solid, liquid or semi-solid form or may comprise a thermosensitive formulation. The agent formulation may comprise a pharmaceutically acceptable carrier in addition to the active agent, with the agent being dispersed homogeneously or heterogeneously within the carrier.

Container 6 or 64 may comprise a composition that is semipermeable, that is, it is permeable to fluid but impermeable to active agent and other ingredients contained in the dispensing device, or it may, alternately, comprise a composition that is impermeable to the exchange of fluid, agent and other ingredients. When an active agent or an active agent dosage form is sensitive to fluid from an exterior fluid present in the environment of use, it is preferred that container 6 or 64 be substantially impermeable to the ingress of the external fluid to serve as a means for substantially protecting the agent or dosage form until it is expelled from housing 2 or 50 and delivered into the environment of use.

Because expandable driving member 10 operates by the imbibition of external fluid, housing 2 in at least a portion that is adjacent to driving member 10 must be permeable or semipermeable; that is, it is permeable to the passage of fluid while being substantially impermeable to the passage of other ingredients contained in the dispensing device.

Housing 2 and container 6 optionally comprise additional ingredients such as, for example, a plasticizer. Semipermeable and impermeable materials suitable for the container and the housing of this invention are known in the art, examples of which are disclosed in U.S. Pat. Nos. 4,874,388 and 5,023,088, the entire disclosures of which are incorporated herein by reference.

Housing 2 and container 6 are nontoxic, biologically inert, nonallergenic and nonirritating to body tissue, and they maintain their physical and chemical integrity; that is, they do not erode or degrade in the environment of use during the dispensing period. It is within the scope of the invention that the housing and container be insoluble only during the period of intended use and can thereafter dissolve away in the environment of the device. Thus, a dispenser is here contemplated which is unaffected by its environment, solubility-wise, at the situs of use or which, alternatively, is only slightly soluble during the period of intended use, such that once its active agent content has been removed it will then dissolve or erode away leaving no objectionable residue or empty container at the situs of use.

The expansion means or expandable driving member 10, operable for separating the housing and the drug unit to release the active agent from the dispensing device of the invention, is nontoxic, nonallergenic and biologically inert. Examples of expansion means useful as the driving member are known in the art and are discussed in U.S. Pat. No. 5,023,088, for example. Driving member 10 comprises, in one presently preferred embodiment, an osmopolymer. The osmopolymers interact with water and aqueous biological fluids and swell or expand to an equilibrium state. The osmopolymers exhibit the ability to swell in fluid and to retain a significant portion of the imbibed and absorbed fluid within the polymer structure. The driving member 10 in another preferred embodiment comprises an osmagent. The osmagents are known also as osmotically effective solutes and they are also known as osmtocially effective compounds. The osmagents that can be used for the purpose of this invention include inorganic and organic compounds that exhibit an osmotic pressure gradient across a semipermeable, i.e. a fluid-permeable, wall. The driving member 10 in yet another preferred embodiment comprises an osmagent dispersed within an osmopolymer. The expandable driving member 10 can comprise a tablet or a layer, or a plurality of tablets or layers, or it can be pressed into housing 2. The osmagent or osmopolymer can be in any suitable form such as particles, crystals, pellets, granules, and the like, when pressed into a tablet layer and into housing 2. Osmagents and osmopolymers are known to the art and are described in, for example, U.S. Pat. Nos. 3,865,108, 4,002,173, 4,207,893, 4,327,725 and 4,612,008.

Partition layer 12, 68, 70, 72 or 74, for example, present between the active agent unit and the driving member, is a means for transmitting the force generated by the expandable driving member against the active agent unit, 4 or 52 for example, for maintaining the separate identity of the active agent formulation and the driving member, and for substantially restricting the passage of fluid between the active agent formulation and the driving member. Representative materials useful as a partition layer are known to the art in, for example, U.S. Pat. No. 4,874,388.

The pharmaceutically acceptable carrier useful herein may comprise more than one ingredient, such as, for example, a buffer, a viscosity regulating vehicle, a surfactant, dyes, a permeation enhancer, proteinase inhibitors, or other formulation ingredients and additives, as are known in the art. The carrier may contain more than one active agent. The active agent formulation can erode or disintegrate and can be in the form of a wax formulation, solid core or tablet, for example. The formulation can immediately dissolve upon exposure to fluid or it may erode slowly with or without the presence of excipients for controlling erosion.

The active agent formulation can be designed in a multitude of ways to provide a specific drug delivery profile. One embodiment may comprise a formulation that contains a biologically acceptable solid surfactant which is capable of slow dispersion in the environmental fluid. In another embodiment, the formulation may contain a fluid-insoluble wax and a surfactant so that the formulation is susceptable to erosion in the environment. In still another embodiment, the formulation may be effervescent and provide drug delivery in a finely dispersed form. This is accomplished by the addition of a solid basic compound capable of evolving carbon dioxide in the presence of an acid in the environment of use. Suitable basic compounds are disclosed in U.S. Pat. No. 4,265,874. In a further embodiment, the formulation may include an osmotic agent or solute, such as those described herein with reference to the expansion means, so that when the formulation comes into contact with the environmental fluid, it immediately dissolves. In yet another embodiment, the agent formulation can be comprised of an agent and a thermoresponsive composition. In this manner, the formulation would exhibit solid-like properties at room temperature of 21° C. and within a few degrees Celsius thereof, and would have a melting point that approximates mammalian body temperatures of 37° C. and within a few degrees Celsius thereof. The term "thermoresponsive" as used herein in a preferred embodiment denotes the physical-chemical property of an agent carrier composition to exhibit solid, or solid-like properties at temperatures up to 31° C. and become fluid, semi-solid or viscous when disturbed by heat at temperatures from 31° C., usually in the range of 31° C. to 45° C. Suitable materials useful as active agent carriers and excipients are known in the art and are disclosed in U.S. Pat. Nos. 4,595,583 and 4,874,388, for example.

Figure 4:
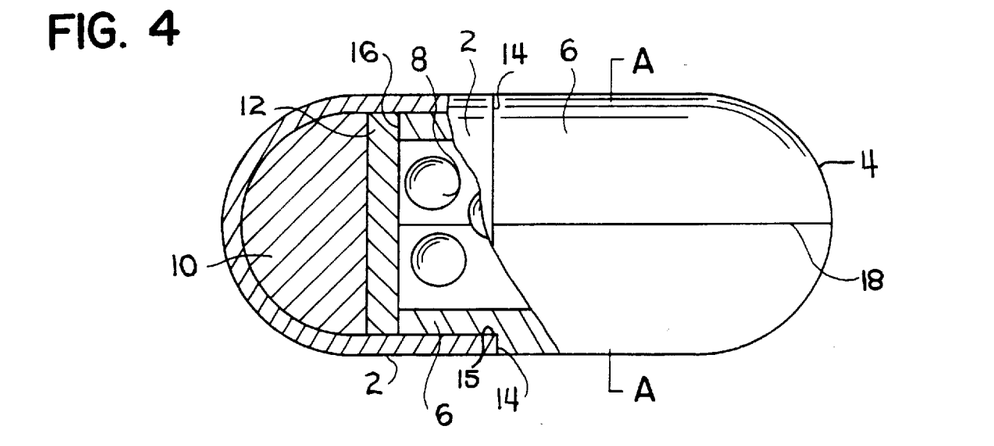
FIG. 4 is a partial cross-sectional view of another embodiment of the invention, having an active agent unit with a wall of two longitudinal halves.

FIG. 4 illustrates, in partial cross-sectional view, a device similar to the devices described in FIGS. 2 and 3 and having a housing 2 with an exit port 15, one drug unit 4 comprised of a container 6 and a plurality of drug dosage forms 8, driving member 10, partition layer 12, receiving means 14 and ridge 16. FIG. 4 illustrates an alternative embodiment of the present invention where container 6 of drug unit 4 is comprised of two longitudinal halves which contact each other at longitudinal junction 18. It is to be noted that, while two longitudinal portions are presented by way of illustration, the invention is not limited thereto, and container 6 of drug unit 4 may be comprised of from one to four or more longitudinal portions. The two longitudinal halves are held together by the pressure exerted on them by that portion of exit port 15 of housing 2 that overlaps the open end 16 of the container 6 of drug unit 4. When the housing and drug unit are separated by the action of the driving member 10, the two longitudinal halves of drug unit 4 become free of the restraining pressure of housing 2 so that the two longitudinal halves can then separate from each other to provide additional exposure of active agent formulation into, or to aid in the release of the active agent formulation to, the environment of use.

Figure 5A:
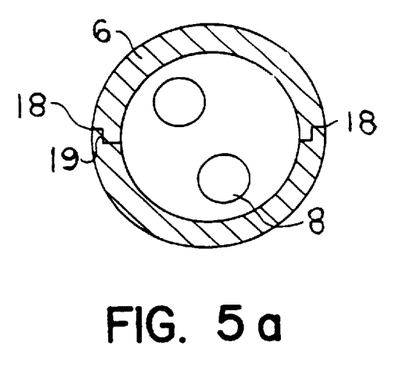
FIGS. 5a and 5b are views through the first wall section of the embodiment of FIG. 4 along line A—A.
Figure 5B:
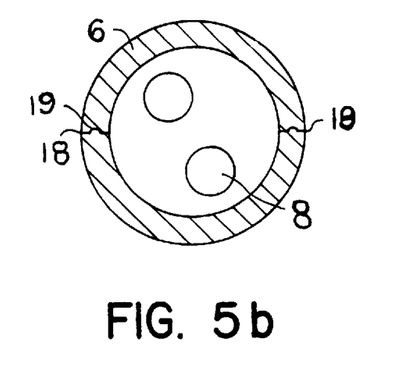

As illustrated in FIGS. 5a and 5b, which are section views along line A—A of the dispensing device of FIG. 4, the longitudinal walls of the two halves of container 6 of drug unit 4 may be so shaped as to provide an interlocking means 19 between the two halves at the longitudinal junction 18. The interlocking means 19 may be, for example, an interlocking ridge that runs continuously along the length of the longitudinal walls of the two halves (FIG. 5a) or a plurality of interlocking concave and convex structures positioned at corresponding points along the longitudinal walls of the two halves (FIG. 5b). The interlocking means 19 provides an additional mechanism for maintaining the two longitudinal halves together while the device is in closed form.

The dispensers of FIGS. 1, 2 and 4 are well-suited to providing an initial delay in the delivery of an active agent to an environment of use. The container 6 or 64 protects the active agent or drug from being disbursed into the environment until such time as the entire unit has been displaced from the device.

The total delay time prior to separation of the dispensing device and delivery of the active agent formulation can be controlled by a number of means. For example, the rate of fluid imbibition into the driving member can be controlled by the particular choice of semipermeable membrane. The rate of expansion of the driving member can be controlled by the choice of composition of the driving member. The distance of overlap between the open end portion of the drug unit or units and the exit means portion of the housing can determine the period of time required for the drug unit to separate from the housing. Combinations of such means may be used. Such control means are known in the art and can be determined without undue experimentation.

The amount of active agent employed in the delivery device will be that amount necessary to deliver a therapeutically effective amount of the agent to achieve the desired result at the site of delivery. In practice, this will vary widely depending upon the particular agent, the site of delivery, the severity of the condition, and the desired therapeutic effect. Thus, it is not practical to define a particular range for the therapeutically effective amount of active agent incorporated into the device.

For proper delivery of the active agent, it may be desirable in some instances for the dispensing device of the present invention to deliver active agent to a particular environment of use. Thus, it may be necessary for the device to remain in a particular environment of use until such time as the agent formulation has been delivered or, alternatively, for the device to pass through one particular environment to another prior to delivering agent formulation. In such cases, additional elements are included in the device, or the device is designed in such a way to provide for such particular delivery. For example, when the environment of use is the rumen of a ruminant animal, a density element may be included in the dispensing device so that the device is weighted to remain within the rumen during the dispensing period. For ruminal systems, an important criteria is that the system remain in the rumen of an animal over a prolonged period of time. This is accomplished by placement of a density element within the dispenser. The housing itself may be the density element. Alternately, one of the partitions can act as the density element. In still another embodiment, one of the drug units can be a density element, placed so as to remain within the housing after all of the drug-containing units have been dispensed. The density element suitable for use in the dispenser of this invention must be dense enough to retain the dispenser in the rumen-reticular sac of a ruminant. The presence of a density element allows the dispenser to remain in the rumen over a prolonged period of time rather than letting it pass into the alimentary tract and be eliminated therefrom. As the dispenser remains in the rumen, a beneficial agent can be delivered to the ruminant at a controlled rate over an extended period of time. Density elements are known in the art and are discussed in, for example, U.S. Pat. Nos. 4,874,388 and 5,023,088.

When the environment of use is the human stomach, it may be desirable for the device to, for example, have a low initial density or to include air in that portion of the internal compartment of the device that also contains the agent formulation. In this manner, the device will float on the surface of the stomach contents and remain in the stomach until the device opens to release the formulation. Where it is desirable, on the other hand, to delay the release of an active agent which, for example, is inactivated by the stomach contents or may cause nausea or bleeding by irritating the gastric mucosa so that delivery in the stomach is not desired, an enteric coating can be applied over at least that portion of the housing of the dispensing device that is comprised of a semipermeable membrane. Enteric coatings will remain intact in the stomach but will rapidly dissolve once they arrive at the small intestine, thereafter allowing fluid to be imbibed to activate the dispensing device. Enteric coatings are well known in the art and are discussed at, for example, *Remington's Pharmaceutical Sciences*, Mack Publishing Co., Easton, Pa.; and *Polymers for Controlled Drug Delivery*, Chapter 3, CRC Press, 1991.

The above description has been given for ease of understanding only. No unnecessary limitations should be understood therefrom, as modifications will be obvious to those skilled in the art.

The following examples are merely illustrative of the present invention and they should not be considered as limiting the scope of the invention in any way, as these examples and other equivalents thereof will become apparent to those versed in the art in the light of the present disclosure, the drawings and the accompanying claims.

EXAMPLE 1

The dispenser of FIG. 1 is especially suited for treatment of helminth infections in ruminants, specifically cattle. Depending upon the nature of delivery desired, several drug formulations can be used in this dispenser.

A suitable drug formulation is comprised of about 80 weight percent Hapadex®, which is an anthelmintic agent for cattle sold by Schering-Plough Corporation. About 0.5 grams of the formulation 66 is compressed into cap 64 to form unit 52. Units 54, 56 and 58 are also filled with the drug formulation. However, if an off period is desired, units 52 and 56 can contain drug and the alternate units 54 and 58 can be empty.

For fast pulse delivery of Hapadex®, the drug formulation is 100% drug. However, this system can be designed to provide a short-duration pulse where the drug formulation has a gas generator contained therein. Especially suitable is a formulation comprised of about 80% Hapadex® and about 20% citric acid/sodium bicarbonate.

If a longer period of delivery is desired, a disintegrating agent such as Ac-Di-Sol® (FMC Corporation), otherwise known as croscarmellose sodium, can be incorporated into the drug formulation in an amount up to 20 weight percent.

For even longer duration of drug delivery, the drug formulation can be 80% Hapadex® and 20% polymer, such as Polyox® (polyethylene oxide polymers) or hydroxypropylmethylcellulose.

EXAMPLE 2

A delivery device according to the invention and as illustrated in FIG. 2 was prepared as follows.

The osmotic engine portion of the device is a compressed bilayer tablet composed of a 150 mg polymeric osmotic formulation (fluid-activated driving member) and a 50 mg wax-based barrier.

The polymeric osmotic formulation has a composition of 60 wt % polyethylene oxide (Polyox® 303, Union Carbide), 29 wt % sodium chloride, 5 wt % polyacrylic acid (Carbomer® 934P, B. F. Goodrich), 5 wt % hydroxypropylmethylcellulose E-5, and 1 wt % ferric oxide. During preparation, each of the above components was screened through a 40 mesh screen, and the sized components were added to a mixing vessel in the appropriate proportions. The dry components were mixed thoroughly for 10 minutes; then, SDA 3A ethanol was slowly added while mixing continued until a wet mass had formed. The wet mass was then screened through a 20 mesh screen, and the wet granules were allowed to air dry for 18 hours. After drying, the granules were passed once more through a 20 mesh screen.

The wax barrier has a composition of 95 wt % microcrystalline wax (MF-2JH Durawax®, Astor Wax Corp.) and 5 wt % gelatin (Type A, 275–300 bloom). During preparation, each component was screened through a 40 mesh screen before being added in the correct weight ratio to a mixing vessel. The dry materials were mixed thoroughly for 10 minutes; then, purified water was slowly added to the mixture while stirring continued. After a wet mass formed, the mixture was passed through a 20 mesh screen, and the granules were oven-dried at 40° C. for 24 hours. After the granules had dried, they were rescreened through a 20 mesh screen.

The osmotic formulation and the wax barrier formulation were compressed in a hydraulic or rotary press into a cylindrical bilayer tablet. The osmotic face of the tablet was convex, to conform to the shape of the delivery device, while the barrier face of the tablet was flat. Tabletting was conducted to produce a clean, distinct interface between the two layers.

To prepare the container of the active agent unit portion (vessel) of the device, 70 wt % cellulose acetate 320 and 30 wt % polypropylene glycol were thoroughly mixed together and were then added to the hopper of a screw extruder. The polymeric mixture was heated at 127° C. as it was extruded through the heated barrel of the extruder and into a mold for the vessel. The polymer mixture was allowed to cool after injection into the mold, after which the container was removed from the opened mold.

The housing of the device was prepared in the same manner as the active agent unit container, the composition of the cap being 70 wt % cellulose acetate 320 and 30 wt % polypropylene glycol. The heated polymeric mixture was injected into a mold for the housing and allowed to cool, and the finished housing was then ejected.

To assemble the delivery device, the desired active agent formulation is placed into a completed agent unit container by manual or automated fill mechanisms. The osmotic engine bilayer tablet is placed into a completed housing with the convex osmotic layer pointed into the closed end of the housing and the barrier layer exposed toward the housing opening. The open end of the filled active agent unit is fitted inside the open end of the housing, and the two pieces are compressed together until housing, osmotic bilayer tablet and agent unit fit together tightly.

EXAMPLE 3

A delivery device was prepared as in Example 2, except that the polymeric osmotic formulation was 130 mg. The assembled device was then coated with approx. 20 mg of a methacrylic acid copolymer enteric coat (Eudragit® L 100-55, Röhm Pharma).

EXAMPLE 4

A delivery device according to the present invention and similar to that illustrated in FIG. 2 was prepared as follows.

The housing was formed by coating a gelatin capsule with a cellulose acetate-based membrane in the following manner. A coating solution composed of 5 wt % cellulose acetate 398 and polyethylene glycol 3350 (in a 95/5 weight ratio) in a solution of acetone/ethanol (in a 90/10 weight ratio) was sprayed onto a size "0" clear gelatin capsule in a Wurster coater. The capsule was coated to a membrane thickness of 3–4 mil. The capsule was then dried in a 50° C. oven to remove residual solvent, after which the two parts of the capsule were separated with their respective membrane covering intact. The short segment of the coated capsule was retained as the required housing, while the long segment was discarded.

The container of the active agent unit portion was formed by machining a cylindrical container with one open end from polycarbonate polymer. The machined dimensions were such that the open end of the agent unit container will fit snugly within the coated gelatin housing.

To assemble the device, following the procedure of Example 2, the osmotic engine bilayer tablet from Example 2 was placed in the housing portion, the desired active agent formulation was placed in the active agent unit container portion, the open end of the agent unit portion was fitted into the open end of the housing portion, and the two pieces were compressed together to obtain a tight fit.

Another device was prepared following the above procedures, except that during manufacture of the housing portion, the gelatin capsule was coated with a cellulose acetate/polyethylene glycol membrane of 8–9 mil thickness.

EXAMPLE 5

Delivery devices were prepared as in Example 4, except that the weight ratio of cellulose acetate to polyethylene glycol in the membrane covering the housing portion was 80/20.

EXAMPLE 6

Nine devices from Example 2, but not containing any active agent formulation, were assembled and placed in artificial intestinal fluid (USP XIX, intestinal fluid, simulated, TS; modified herein by not including enzymes) in a shaker bath at 37° C. Marbles were also added to the fluid to provide abrasion with the devices, simulating an intestinal environment. The devices were observed to determine when the housing and active agent unit portions separated from each other. The resulting average release point for the devices was at 3.84 hours (SD=0.18 hr).

EXAMPLE 7

Two enteric-coated devices from Example 3, but not containing any active agent formulation, were assembled and placed in artificial gastric fluid (USP XIX, gastric fluid, simulated, TS; modified herein by not including enzymes) for 2 hours, after which they were removed from the gastric fluid and placed in artificial intestinal fluid. The devices were observed in the intestinal fluid to determine when the housing and active agent unit portions separated. The resulting average release point for the two devices was at 6.33 hours.

EXAMPLE 8

Four devices from Example 4 having a housing membrane thickness of 3–4 mil and containing cardizem pellets as the active agent formulation were placed in artificial intestinal fluid and observed for separation. The devices separated and the cardizem pellets were released to the fluid environment at an average time of about 1.4 hours after placement in the fluid.

In the same manner, three devices from Example 4 having a housing membrane thickness of 8–9 mil and containing cardizem pellets were placed in the artifical intestinal fluid environment. The devices separated and the cardizem pellets were released at an average time of about 7.1 hours after placement.

EXAMPLE 9

Five devices from Example 4 having a housing membrane thickness of 8–9 mil and containing cimetidine granules as the active agent formulation were placed in artificial intestinal fluid and observed for separation. The devices separated and the cimetidine granules were released to the fluid environment at an average time of about 6.4 hours after placement in the fluid.

EXAMPLE 10

A delivery device according to the present invention and similar to that illustrated in FIG. 2, containing calcitonin, was prepared as follows.

The housing was formed by coating a size "0" gelatin capsule, according to the procedures of Example 4, with 54 mg of a semipermeable membrane comprised of 60 wt % cellulose acetate 398-10 and 40 wt % hydroxypropylcellulose (Klucel® EF), the short segment of the coated capsule being retained as the required housing.

The container of the active agent unit was formed by machining a cylindrical container with one open end from ethylene vinyl acetate copolymer, having 9% vinyl acetate. The machined dimensions were such that the open end of the drug unit container will fit snugly within the coated gelatin housing and the inside dimensions will contain 110 mg of a calcitonin formulation.

The calcitonin formulation has a composition of 0.91 wt % calcitonin, 0.18 wt % sodium citrate, 0.28 wt % anhydrous citric acid, and 98.63 wt % mannitol.

An osmotic engine bilayer tablet was made following the procedures of Example 2, except that the polymeric osmotic formulation has a composition of 59.65 wt % Polyox® 303, and in addition to the other ingredients also has 0.25 wt % magnesium stearate and 0.10 wt % BHT and the wax barrier has a composition of 90 wt % microcrystalline wax (MF-2JH Durawax®) and hydroxypropylcellulose (Klucel® HF). The resulting bilayer tablet contained 150 mg of the osmotic formulation and 60 mg of the wax barrier formulation.

To assemble the device, following the procedure of Example 2, the osmotic engine bilayer tablet was placed in the housing, the calcitonin formulation (110 mg) was placed in the active agent unit container, the open end of the housing was fitted into the open end of the drug unit, and the two pieces were compressed together to obtain a tight fit.

EXAMPLE 11

Figure 6:
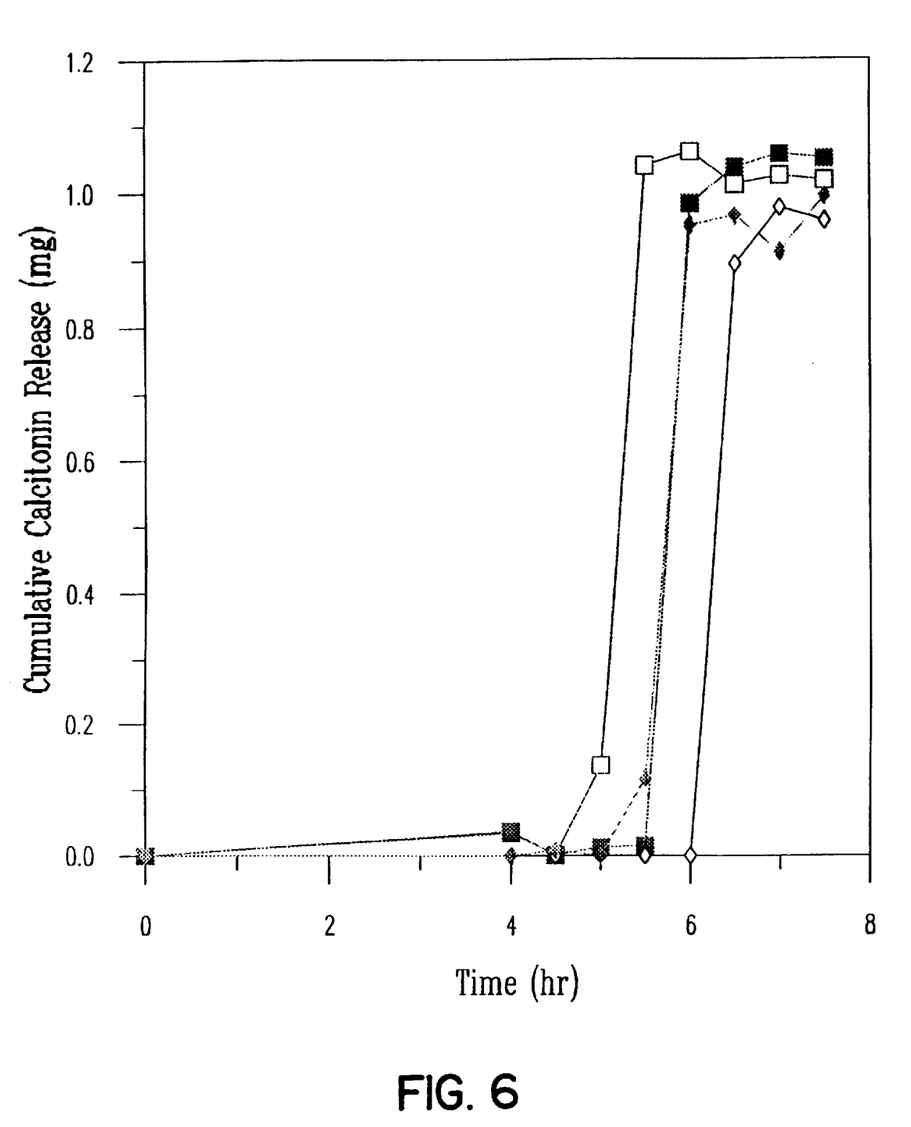
FIG. 6 shows the release profile of calcitonin from a device of the present invention.

Four delivery devices similar to the device of Example 10, containing 1 mg of calcitonin and having a housing membrane thickness of approx. 6 mils, were tested for release of calcitonin using the USP paddle method (at 150 rpm). The devices were placed in 500 mL of pH 4 solution with 0.1% bovine albumin and stirred. The devices were observed to determine when the housing and drug unit separated from each other, and the solution was then tested for presence of calcitonin to confirm the drug release time and the duration of release. The results are shown in FIG. 6 and indicate that each device released its content completely after 4 to 6 hours and over a short duration of time of less than half an hour.

This invention has been described in detail with particular reference to certain preferred embodiments thereof, but it will be understood that variations and modifications can be effected within the spirit and scope of the invention.

What is claimed is:

1. A dispensing device for dispensing an active agent to a fluid environment of use, the dispensing device comprising:

(a) a housing and a container in sliding telescoping relation with each other, the housing comprising an open end and a fluid-passing portion opposite the open end, said fluid-passing portion permitting passage of fluid into the housing, and the container comprising an open end, wherein said container open end is disposed within said housing open end to form a closed unit;

(b) an active agent formulation comprising an active agent within said container;

(c) a fluid-activating driving member within said housing, in fluid-transmitting relationship with the fluid-passing portion of the housing, said fluid-activated driving member expanding as it imbibes fluid thereby effecting separation of the housing and container of the closed unit, for providing a sharp pulsed release of the active agent formulation to the fluid environment of use; and (d) optionally, a partition layer between the driving member and the container open end.

2. A dispensing device according to claim 1 wherein the container is comprised of a substantially fluid impermeable composition.

3. A dispensing device according to claim 1 wherein the active agent formulation comprises a plurality of dosage forms.

4. A dispensing device according to claim 3 wherein the plurality of dosage forms contain the same active agent.

5. A dispensing device according to claim 3 wherein the plurality of dosage forms contain different active agents.

6. A dispensing device according to claim 1 wherein the active agent is selected from the group consisting of proteins and peptides.

7. A dispensing device according to claim 1 wherein the active agent is calcitonin.

8. A dispensing device according to claim 1 which further comprises an enteric coating.

9. A dispensing device according to claim 1 wherein the container comprises two or more longitudinal portions.

10. A dispensing device according to claim 9 wherein the longitudinal portions comprise interlocking junctions.

* * * * *